United States Patent
Tseng

(10) Patent No.: US 11,537,460 B1
(45) Date of Patent: Dec. 27, 2022

(54) DISPLAYING EQUIPMENT AND DISPLAYING METHOD CAPABLE OF QUICK DISPLAYING AND SYSTEM-FAILURE BACKUP MECHANISM

(71) Applicant: ML TECHNOLOGY LTD., New Taipei (TW)

(72) Inventor: Ying-Chang Tseng, New Taipei (TW)

(73) Assignee: ML TECHNOLOGY LTD., New Taipei (TW)

( * ) Notice: Subject to any disclaimer, the term of this patent is extended or adjusted under 35 U.S.C. 154(b) by 0 days.

(21) Appl. No.: 17/564,817

(22) Filed: Dec. 29, 2021

Related U.S. Application Data

(60) Provisional application No. 63/223,562, filed on Jul. 20, 2021.

(51) Int. Cl.
 *G06F 11/00* (2006.01)
 *G06F 11/07* (2006.01)
 (Continued)

(52) U.S. Cl.
 CPC .......... *G06F 11/0733* (2013.01); *G02B 23/24* (2013.01); *G06F 3/147* (2013.01);
 (Continued)

(58) Field of Classification Search
 CPC .. G06F 9/4401; G06F 9/4406; G06F 11/0733; G06F 11/0757; G06F 11/1417;
 (Continued)

(56) References Cited

U.S. PATENT DOCUMENTS 11,099,339 B1 * 8/2021 Wingrove .......... H04B 10/0795
2016/0345057 A1 * 11/2016 Tago .................. H04N 21/4437

FOREIGN PATENT DOCUMENTS

JP 2009195622 A * 9/2009
TW 201142696 A 12/2011
(Continued)

OTHER PUBLICATIONS

Machine Translation of JP 2009195622 A (Year: 2009).*
Office Action dated Apr. 25, 2022 of the corresponding Taiwan patent application No. 110135617.

*Primary Examiner* — Michael Maskulinski
(74) *Attorney, Agent, or Firm* — Chun-Ming Shih; HDLS IPR Services

(57) ABSTRACT

A displaying equipment at least including an image controlling module, a primary system module, and a system controlling module is disclosed. The image controlling module continuously receives an input image from an image sensitive device after activates, and directly outputs the received input image. The system controlling module constantly monitors the primary system module after activates to determine whether the primary system module activates completely. The primary system module runs an operating system after being activated to process the input image and to generate a processed image. After the primary system module activates completely, the image controlling module outputs both the input image and the processed image simultaneously. When the primary system module is abnormal, the image controlling module restores to output the input image only.

14 Claims, 8 Drawing Sheets

(51) Int. Cl.
*G06F 3/147* (2006.01)
*G06F 11/14* (2006.01)
*G02B 23/24* (2006.01)
*G06F 11/20* (2006.01)

(52) U.S. Cl.
CPC ...... *G06F 11/0757* (2013.01); *G06F 11/1441* (2013.01); *G06F 11/202* (2013.01)

(58) Field of Classification Search
CPC .. G06F 11/1441; G06F 11/162; G06F 11/202; G06F 11/2023; G06F 11/3485; G06F 2211/1097; G02B 23/24
See application file for complete search history.

(56) References Cited

FOREIGN PATENT DOCUMENTS

| | | |
|---|---|---|
| TW | 201800057 A | 1/2018 |
| TW | M564193 U | 7/2018 |

\* cited by examiner

DISPLAYING EQUIPMENT AND DISPLAYING METHOD CAPABLE OF QUICK DISPLAYING AND SYSTEM-FAILURE BACKUP MECHANISM

CROSS-REFERENCE TO RELATED APPLICATION

This patent application claims the benefit of United States Provisional Patent Application No. 63/223,562, filed Jul. 20, 2021, which is incorporated by reference herein.

BACKGROUND OF THE DISCLOSURE

Technical Field

The present disclosure relates to a displaying equipment and a displaying method, and specifically relates to a displaying equipment and a displaying method capable of quick displaying and system-failure backup mechanism.

Description of Related Art

Generally, an image processing system may analyze images produced and generated by image sensitive devices such as endoscopes and ultrasonic probes, etc., so that the users may see and check these images more easily and clearly.

To perform the above actions, the image processing system needs to run an operating system (OS), and then executes the essential algorithm(s) and application program(s) correspondingly by the OS. Therefore, this type of image processing system needs a longer boot time in comparison with other types of image processing system. However, under some special circumstances (e.g., an emergency medical action), the user (such as a doctor) needs the images sensed and generated from the image sensitive devices immediately, and he or she cannot waste the time for the long boot time of the image processing system.

The common image processing systems in the market usually execute a specific OS and a specific application program(s). When the image processing systems is overloaded, the images may either be generated unstably or be frozen, or the image processing systems may crash directly. If the user is having an emergency medical action but cannot obtain the demanded images continuously and stably, the consequence may be vital.

Therefore, the image processing systems in the market need a further improvement.

SUMMARY OF THE DISCLOSURE

The present disclosure is directed to a displaying equipment and a displaying method capable of quick displaying and system-failure backup mechanism, which can provide an output image immediately right after the displaying equipment activates, and keep providing the output image stably even when the primary system of the displaying equipment is overloaded or crashes.

In one of the exemplary embodiments, the displaying equipment includes:

an image input port, connected to an image sensitive device to continuously receive an input image;

an image output unit;

an image controlling module, connected with the image input port and the image output unit, and configured to continuously receive the input image from the image input port and immediately control the image output unit to continuously output the input image after the image controlling module activates completely;

a primary system module, connected with the image controlling module, configured to run an operating system (OS) after being activated, and configured to perform an image processing procedure to the input image to generate a processed image, and to continuously transmits the processed image to the image controlling module, wherein an activation completing time of the primary system module is later than or equal to an activation completing time of the image controlling module; and a system controlling module, connected with the image controlling module and the primary system module, configured to continuously monitor the primary system module after the system controlling module activates completely;

wherein, the image controlling module is configured to control the image output unit to output both the input image and the processed image after receiving the processed image, and configured to control the image output unit to only output the input image when the primary system module is determined to be abnormal.

In another embodiment, the displaying method includes following steps:

a) continuously monitoring the primary system module by the system controlling module after the system controlling module activates completely;

b) continuously receiving an input image from an image sensitive device and immediately controlling an image output unit to continuously output the input image by the image controlling module after the image controlling module activates completely;

c) running an operating system (OS) by the primary system module after the primary system module is activated, wherein an activation completing time of the primary system module is later than or equal to an activation completing time of the image controlling module;

d) continuously receiving the input image from the image controlling module, executing an image processing procedure to the input image to generate a processed image, and continuously transmitting the processed image to the image controlling module by the OS;

e) controlling the image output unit to output both the input image and the processed image by the image controlling module after receiving the processed image;

f) determining whether the primary system module is abnormal; and g) controlling the image output unit to only output the input image by the image controlling module when the primary system module is determined to be abnormal.

Once the user connects the image sensitive device to the displaying equipment and activates the displaying equipment of the present disclosure, he or she may obtain the demanded image immediately without waiting for the primary system module of the displaying equipment to activate completely. In addition, even if the primary system module encounters delay or crashes due to its overloading while the user uses the displaying equipment, the displaying equipment may keep providing the output image stably, and there will be no situations in which users cannot obtain images and cannot perform tasks.

DETAILED DESCRIPTION

In cooperation with the attached drawings, the technical contents and detailed description of the present disclosure are described hereinafter according to multiple embodiments, being not used to limit its executing scope. Any equivalent variation and modification made according to appended claims is all covered by the claims claimed by the present disclosure.

The present disclosure discloses a displaying equipment for an emergency medical action (e.g., to perform an inspection or a medical first-aid on the ambulance), and a displaying method incorporated with the displaying equipment. The displaying equipment may immediately output images generated by an image sensitive device right after the displaying equipment is triggered to receive power and boot, so the user (such as a doctor or a nurse, etc.) may immediately obtain the images related to the medical action. In addition, the displaying equipment may keep outputting the images continuously even when the system is overloaded or crashes, and there will be no situations in which the user may stop the medical action because of the technical issue caused by the devices.

Figure 1:
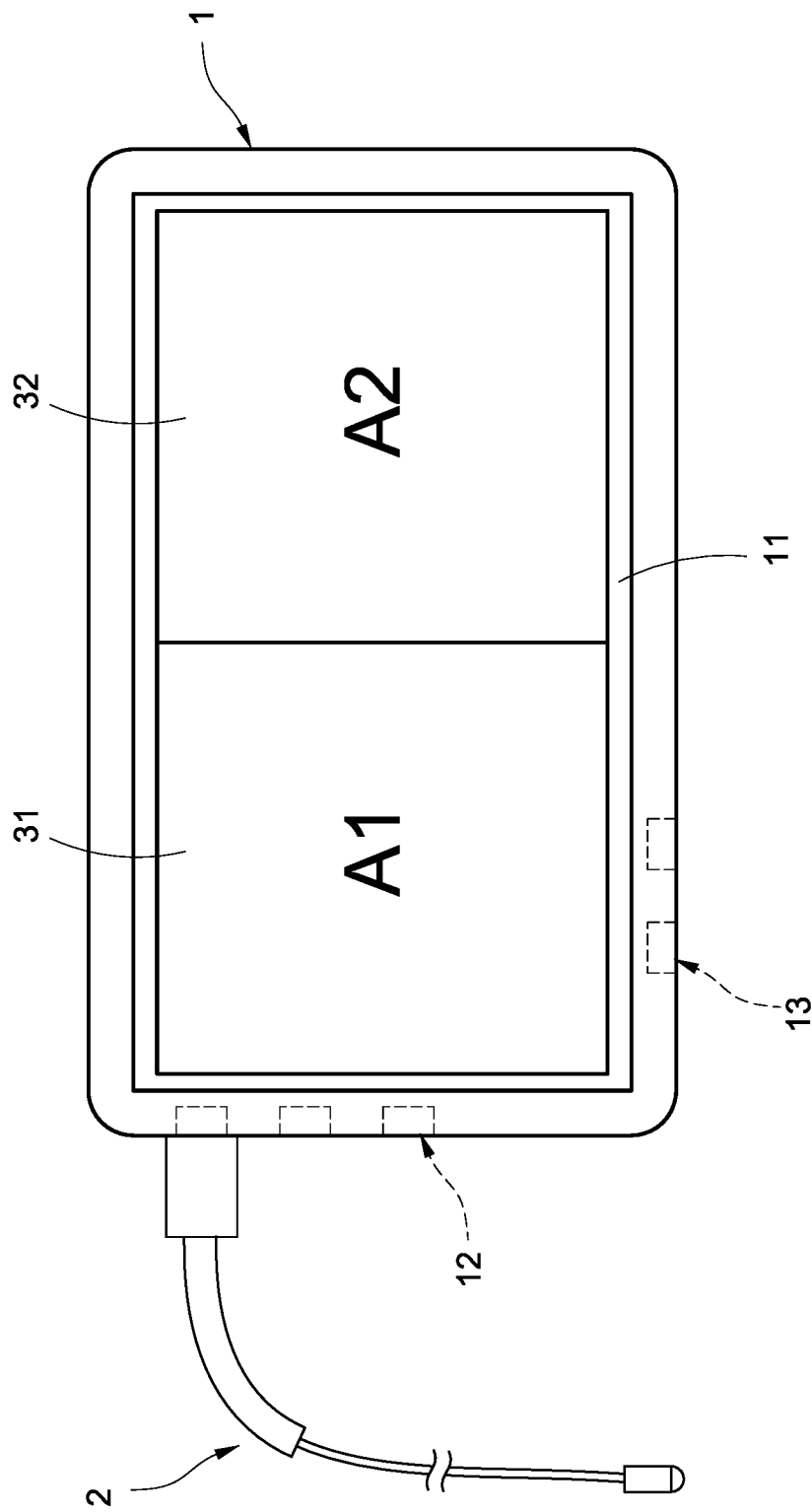
FIG. 1 is a schematic diagram of a displaying equipment of a first embodiment according to the present disclosure.
Figure 2:
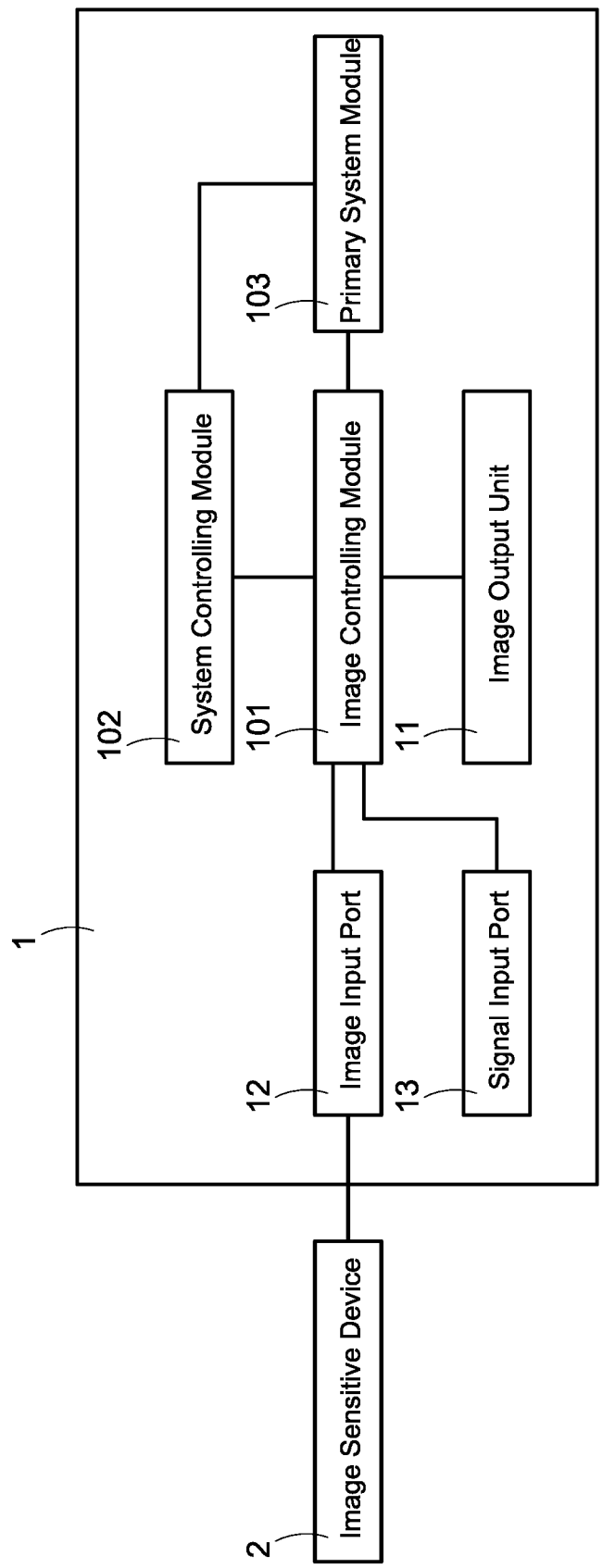
FIG. 2 is a block diagram of a displaying equipment of a first embodiment according to the present disclosure.

Please refer to FIG. 1 and FIG. 2, wherein FIG. 1 is a schematic diagram of a displaying equipment of a first embodiment according to the present disclosure, and FIG. 2 is a block diagram of a displaying equipment of a first embodiment according to the present disclosure.

The present disclosure provides a displaying equipment capable of quick displaying and system-failure backup mechanism (referred to as the displaying equipment 1 hereinafter). As disclosed in FIG. 1, the displaying equipment 1 may be connected with an external image sensitive device 2, such as an endoscope or an ultrasonic probe, etc., but not limited thereto. After receiving an input image sensed and generated by the image sensitive device 2, the displaying equipment 1 performs a necessary process to the received input image through an internal algorithm(s) or application program(s), such as an AI process, an image analysis procedure, an image correcting procedure, or an image editing procedure, etc. Also, the displaying equipment 1 may perform actions like audio recording or video recording, etc. through one of the internal application programs, so as to record a usage process about the user using the image sensitive device 2 and the displaying equipment 1.

To perform the aforementioned algorithms and application programs, the displaying equipment 1 needs to run an operating system (OS), such as Windows, Linux, and Android, etc. through the internal processor, and then executes the demanded algorithms and application programs through the OS. The boot time for the OS usually takes one to five minutes or so; however, under the special circumstances as previously discussed, some users cannot wait for such a long boot time.

In the present disclosure, when the user connects the image sensitive device 2 to the displaying equipment 1 and presses a power button (not shown) of the displaying equipment 1 to activate the displaying equipment 1, the displaying equipment 1 may immediately and directly output, through an image output unit 11 thereon, the image(s) sensed and generated by the image sensitive device 1. Therefore, the problem that the user has to wait for the displaying equipment 1 to completely boot and to run the OS and the application programs under an emergency medical action can be resolved, thereby saving the rescue golden time.

In the embodiment of FIG. 1 and FIG. 2, the displaying equipment 1 includes an image controlling module 101, a system controlling module 102, a primary system module 103, an image output unit 11, and an image input port 12. In the embodiment, the image controlling module 101 is configured to process the images of the displaying equipment 1, the system controlling module 102 is configured to process the signals and the commands of the displaying equipment 1, and the primary system module 103 is configured to execute the OS, the related algorithms, and the related application programs of the displaying equipment 1.

The image input port 12 may be a connecting port, such as a port compatible with a universal serial bus (USB), a serial peripheral interface (SPI), or an I$^2$C, etc., or another port compatible with common video outputting interfaces such as a mobile industry processor interface (MIPI) or a serial digital interface (SDI), but not limited thereto. The displaying equipment 1 is connected with the image sensitive device 2 through the image input port 12, so the displaying equipment 1 may continuously receive an input image (such as the input image 31 shown in FIG. 1) from the image sensitive device 2 after receiving the power and boot. The image sensitive device 2 may be, for example but not limited to, a medical sensor such as an endoscope or an ultrasonic probe, and the input image 31 may be, for example but not limited to, a human-body image sensed and generated by the endoscope or the ultrasonic probe.

In one embodiment, the image output unit 11 may be a video connecting port, such as a high-definition multimedia interface (HDMI) connecting port, a serial digital interface (SDI) connecting port, or a DisplayPort connecting port, etc., but not limited thereto. In the embodiment, the displaying equipment 1 may be connected with an external displayer (not shown) through the image output unit 11, so as to provide and display images.

In another embodiment, the image output unit 11 may be a displayer configured on the displaying equipment 1, so the displaying equipment 1 may directly display the images on the image output unit 11. However, the above description is only one embodiment of the present disclosure, but not limited thereto.

The image controlling module 101 is connected with the image input port 12 and the image output unit 11. The image controlling module 101 may be a module implemented by a combination of hardware and software. In particular, the image controlling module 101 may be implemented by, for example but not limited to, a field programmable gate array (FPGA) or an application specific integrated circuit (ASIC).

If the image controlling module 101 is implemented by the FPGA or the ASIC, the image controlling module 101 may activate completely in a very short time (such as smaller than 100 ms) after the displaying equipment 1 is powered.

In the present disclosure, the image controlling module 101 may start continuously receive the input image 31 through the image input port 12 after activates, and may immediately control the image output unit 11 to output the input image 31. In other words, after the user presses the power button of the displaying equipment 1, the displaying equipment 1 may start to display the input image 31 of the image sensitive device 2 in a very short time (may be smaller than 100 ms).

It should be mentioned that the displaying equipment 1 may include multiple image input ports 12, and may be connected with multiple image sensitive devices 2 to receive multiple input images 31 at the same time. Under such circumstance, the image controlling module 101 may display multiple input images 31 side by side in accordance with a default setting or a control of the system controlling module 102. For the ease of understanding, the following descriptions will be provided with the displaying equipment 1 connecting with only one image sensitive device 2 to receive one input image 31 a time for an example.

In particular, the displaying equipment 1 of the present disclosure uses the primary system module 103 to analyze and process the input image 31 (e.g., to perform the image correcting procedure or the image editing procedure, etc.), so that the user can check the image with ease. However, before the primary system module 103 activates completely, the displaying equipment 1 may directly provide, through the image controlling module 101, the input image 31 without any processing; therefore, the user may obtain the demanded image information in a shortest time.

The system controlling module 102 is connected with the image controlling module 101 and the primary system module 103. The system controlling module 102 may be a module implemented by a combination of hardware and software. In particular, the system controlling module 102 may be implemented by, for example but not limited to, a micro control unit (MCU) or an embedded controller (EC).

If the system controlling module 102 is implemented by MCU or EC, then it is similar to the image controlling module 101. In other words, the system controlling module 102 may activate completely in a very short time (generally shorter than or equal to an activation completing time of the image controlling module 101) after the displaying equipment 1 is powered. In the present disclosure, the system controlling module 102 may constantly monitor the primary system module 103 after the system controlling module 102 activates completely, so as to determine whether the primary system module 103 activates completely or not. In particular, the system controlling module 102 may determine that the primary system module 103 activates completely once the OS and the application program(s) in the primary system module 103 are run and setup completely. In addition, the system controlling module 102 may continuously monitor the primary system module 103 after the primary system module 103 activates completely, so as to determine whether the primary system module 103 encounters overloaded or crashes.

One technical feature of the present disclosure is that after the primary system module 103 activates completely and operates normally, the image controlling module 101 may control the image output unit 11 to display both the input image 31 without any processing and the processed image 32 generated and provided by the primary system module 103 simultaneously. In comparison, before the primary system module 103 activates completely, or when the primary system module 103 activates completely but operates abnormally, the image controlling module 101 controls the image output unit 11 to only display the input image 31 that is an image without any processing. Therefore, no matter what the current status of the primary system module 103 is, the user may obtain the demanded images from the displaying equipment 1.

The primary system module 103 is connected with the image controlling module 101 and the system controlling module 102. The primary system module 103 may be a module implemented by a combination of hardware and software. In particular, the primary system module 103 may be implemented by, for example but not limited to, a central process unit (CPU) or a graphic process unit (GPU).

In one embodiment, the activation completing time for the primary system module 103 to completely activate may be later than or equal to the activation completing time for the image controlling module 101 to completely activate. In particular, the primary system module 103 runs the OS first after receiving power. After the OS runs completely, the primary system module 103 executes one or more preset application programs by the OS. After the one or more application programs are executed and setup completely, the system controlling module 102 determines that the primary system module 103 activates completely.

In one embodiment, the primary system module 103 may send an image requirement to the image controlling module 101 by the OS after the primary system module 103 activates completely, so as to ask the image controlling module 101 to provide the input image 31 to the primary system module 103. In another embodiment, the system controlling module 102 may send a control command to the image controlling module 101 when determining that the primary system module 103 activates completely, so that the image controlling module 101 may start to transmit the input image 31 to the primary system module 103.

The primary system module 103 executes an image processing procedure to the received input image 31 by the executed application program and to generate the processed image 32 correspondingly. The processed image 32 may include a result(s) from the actions like an image analysis procedure, an image correcting procedure, or an image editing procedure, etc. performed to the input image 31. Also, the primary system module 103 continuously transmits the processed image 32 to the image controlling module 101.

Figure 4:
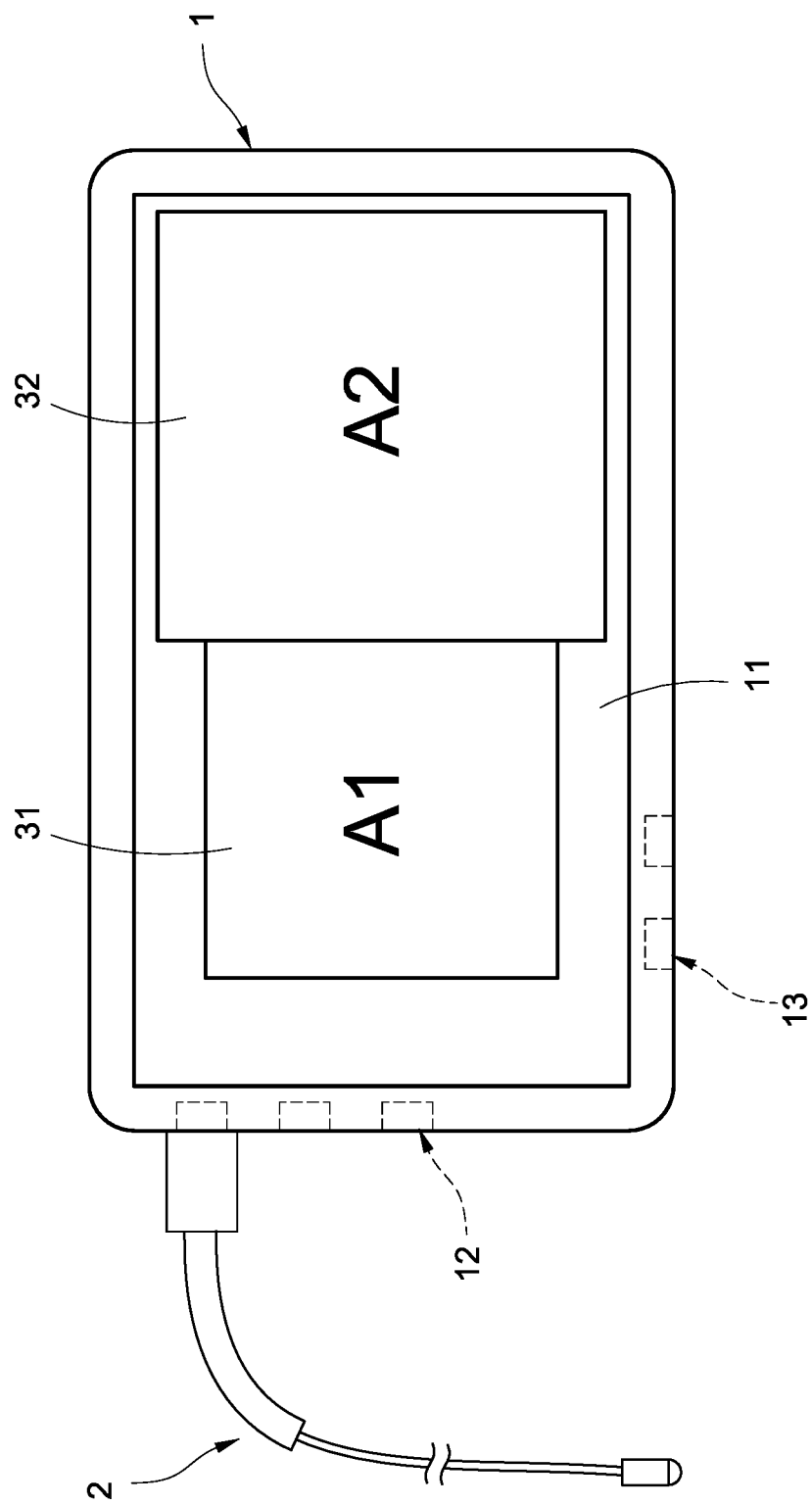
FIG. 4 is a schematic diagram of a displaying equipment of a second embodiment according to the present disclosure.

In the present disclosure, the image controlling module 101 continuously receives the input image 31 from the image sensitive device 2 after it activates completely, and the image controlling module 101 controls the image output unit 11 to immediately output the input image 31 alone. After the image controlling module 101 starts to receive the processed image 32 from the primary system module 103, the image controlling module 101 controls the image output unit 11 to switch and to output both the input image 31 and the processed image 32 at the same time. In particular, the image output unit 11 may display the input image 31 and the processed image 32 side by side (e.g., to use a display mode as shown in FIG. 1), or display the input image 31 and the processed image 32 superimposed with each other (e.g., to use a display mode as shown in FIG. 4), but not limited thereto.

If the primary system module 103 encounters abnormality (e.g., the primary system module 103 is overloaded or crashes) and causes the primary system module 103 to produce the processed image 32 unstably or to stop transmitting the processed image 32 to the image controlling module 101, the image controlling module 101 may immediately control the image output unit 11 to restore to output the input image 31 alone. Therefore, the abnormality of the primary system module 103 will not affect the main purpose that is for the user to obtain the demanded images from the displaying equipment 1.

It should be mentioned that the displaying equipment 1 uses same battery set or power source (not shown) to connect the image controlling module 101, the system controlling module 102, and the primary system module 103. When the power button of the displaying equipment 1 is pressed, the image controlling module 101, the system controlling module 102, and the primary system module 103 may be triggered to receive power and to activate at the same time point.

In one embodiment, the system controlling module 102 has the shortest activation completing time. The activation completing time of the image controlling module 101 is later than that of the system controlling module 102, and the activation completing time of the primary system module 103 is later than or equal to that of the image controlling module 101.

Figure 3A:
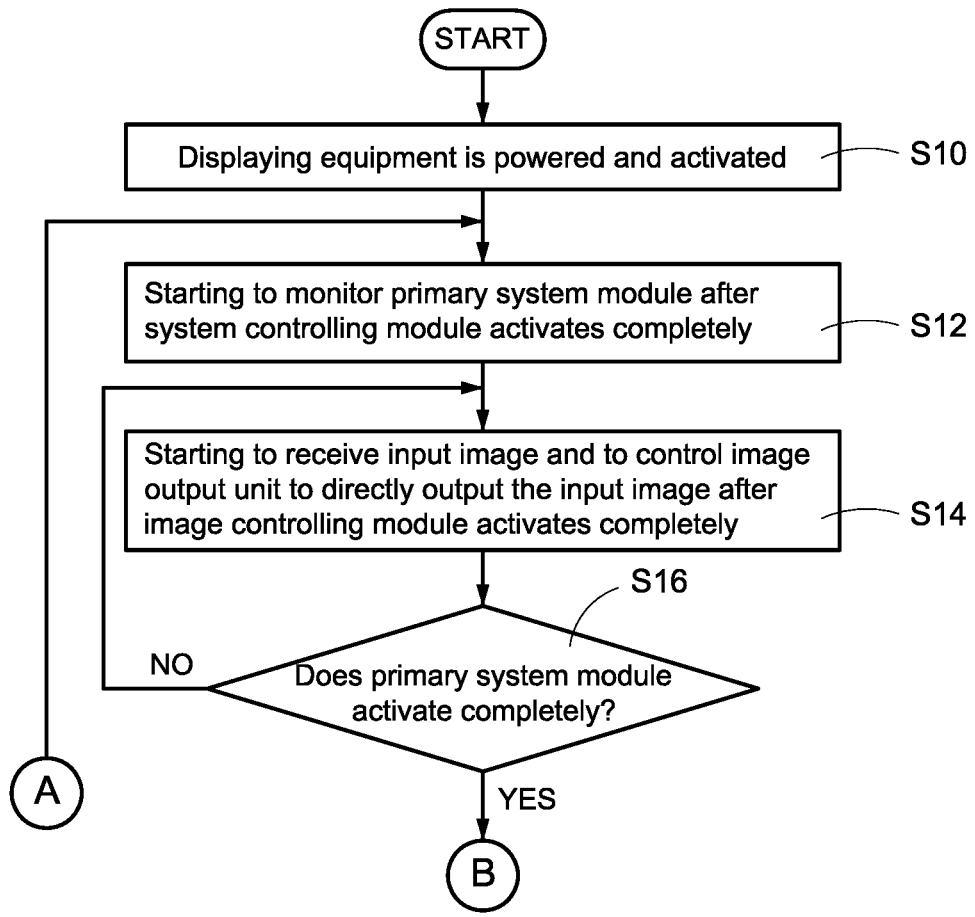
FIG. 3A is a first part of a flowchart showing a displaying method of a first embodiment according to the present disclosure.
Figure 3B:
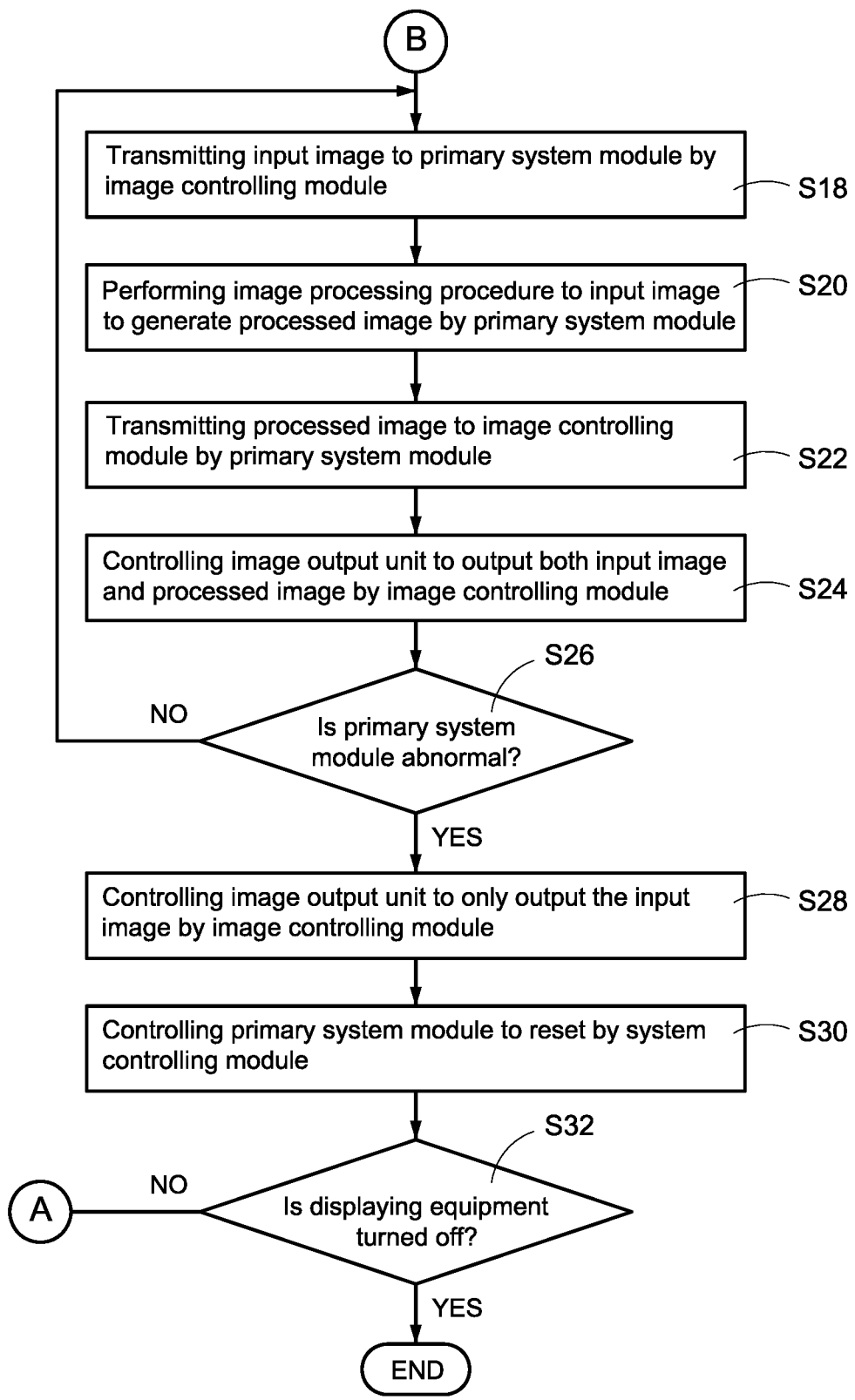
FIG. 3B is a second part of a flowchart showing the displaying method of a first embodiment according to the present disclosure.

Please refer to FIG. 1, FIG. 2, FIG. 3A, and FIG. 3B at the same time, wherein FIG. 3A is a first part of a flowchart showing a displaying method of a first embodiment according to the present disclosure, and FIG. 3B is a second part of a flowchart showing a displaying method of the first embodiment according to the present disclosure. FIG. 3A and FIG. 3B disclose a displaying method capable of quick displaying and system-failure backup mechanism (referred to as the displaying method hereinafter), and the displaying method is incorporated with the displaying equipment 1 as shown in FIG. 1 and FIG. 2.

First, the displaying equipment 1 is powered and activated (step S10). In one embodiment, the displaying equipment 1 is powered and activated after the power button thereon (not shown) is pressed, and the displaying equipment 1 provides power to the image controlling module 101, the system controlling module 102, and the primary system module 103 through a battery set, an internal power source, or an external power source.

In one embodiment, the system controlling module 102 may activate completely before the image controlling module 101 and the primary system module 103. After the system controlling module 102 activates completely, it starts to monitor the primary system module 103 (step S12), so as to determine whether the primary system module 103 activates completely or not.

For example, the system controlling module 102 may execute a watchdog procedure to monitor the primary system module 103, or periodically perform a handshaking procedure with the primary system module 103 to monitor the primary system module 103. If the system controlling module 102 performs the above procedures and the primary system module 103 responds with the calling from the system controlling module 102, the system controlling module 102 may confirm that the primary system module 103 activates completely. In particular, the system controlling module 102 may execute the watchdog procedure or the handshaking procedure to monitor either the primary system module 103 itself, the OS run by the primary system module 103, or the application programs executed by the OS, but not limited thereto.

In one embodiment, the image controlling module 101 may activate completely later than the system controlling module 102 but prior to the primary system module 103. After the image controlling module 101 activates completely, the image controlling module 101 starts to receive the input image 31 from the image sensitive device 2 and to control the image output unit 11 to directly output the received input image 31 (step S14). Through the step S14, the displaying equipment 1 may immediately provide the input image 31 sensed and generated by the image sensitive device 2 through the image output unit 11 in a very short time after the user presses the power button on it. In other words, the user doesn't have to wait for the primary system module 103 to activate completely to obtain the image.

It should be mentioned that after the image controlling module 101 activates completely, the image controlling module 101 may activate the displayer that is currently connected to the displaying equipment 1 (such as the image output unit 11 or an external displayer), and logically plan the display area of the displayer. For example, if there are two image sensitive devices 2 connected to the displaying equipment 1, two display areas are required on the displayer to display two sets of input image 31 respectively received from the two image sensitive devices 2.

After the step S14, the system controlling module 102 continuously determines whether the primary system module 103 activates completely or not (step S16). Before the primary system module 103 activates completely, the displaying equipment 1 continuously executes the step S14, so that the image controlling module 101 and the image output unit 11 continuously receive and output the input image 31.

In particular, the primary system module 103 runs the OS after it is powered and boot. The OS may be, for example but not limited to, Windows, Linus, or Android, etc. After the OS runs completely, the primary system module 103 executes one or more preset application programs by the OS. After all the application programs are executed and setup completely, the primary system module 103 is considered to activate completely.

If the primary system module 103 is determined to activate completely in the step S16, the image controlling module 101, based on the control command sent by the system controlling module 102 or the image requirement sent by the OS of the primary system module 103, starts to transmit the received input image 31 to the primary system module 103 (step S18). After the step S18, the primary system module 103 may perform an image processing procedure to the input image 31 by the one or more executed application programs, so as to generate the processed image 32 correspondingly (step S20). Also, the primary system module 103 continuously transmits the processed image 32 to the image controlling module 101 (step S22).

In one embodiment, the primary system module 103 and the image controlling module 101 may connect with each other through an HDMI connector or a camera input port to transmit the input image 31 and the processed image 32 to each other, but not limited thereto.

After the image controlling module 101 starts to receive the processed image 32 from the primary system module 103, the image controlling module 101 controls the image output unit 11 to switch its display mode from outputting the input image 31 alone to outputting both the input image 31 and the processed image 32 at the same time (step S24).

After the step S24, the user may obtain the input image 31 that is without analyzing, processing, and correcting from the displaying equipment 1, and may also obtain the processed image 32 that is generated by the one or more image processing procedures.

It should be mentioned that the processed image 32 has been analyzed and processed by the application programs of the primary system module 103, so the processed image 32 includes information more than the input image 31 does. In part of the embodiments, the image controlling module 101 in the step S24 may control the image output unit 11 to switch from using a display mode of outputting the input image 31 alone to using another display mode of outputting the processed image 32 alone.

After the step S24, the displaying equipment 1 may continuously determine whether the primary system module 103 is abnormal or not by the image controlling module 101 and/or the system control module 102 (step S26). If the primary system module 103 operates normally, the displaying equipment 1 re-executes the step S18 through the step S24 to continuously display the input image 31 and the processed image 32 through the image output unit 11.

If the primary system module 103 operates abnormally, it may fail in continuously generating and providing the processed image 32, or the processed image 32 provided by the abnormal primary system module 103 may be error or unstable. To prevent the user from misjudgment, the image controlling module 101 may immediately control the image output unit 11 to restore to the display mode of outputting the input image 31 alone whenever the primary system module 103 is determined to be abnormal in the step S26 (step S28). When the primary system module 103 is determined to be abnormal, the system controlling module 102 may force the primary system module 103 to reset through sending a corresponding instruction to the primary system module 103 (step S30).

It should be mentioned that the step S28 and the step S30 do not have an execution order. Otherwise, the displaying equipment 1 may simultaneously executes the step S28 and the step S30 through both the image controlling module 101 and the system controlling module 102 via multitasking technique, but not limited.

Through the execution of the step S28, the displaying equipment 1 will not stop outputting images due to the abnormality of the primary system module 103; therefore, the user may continuously obtain the demanded images sensed and generated by the image sensitive device 2. Through the execution of the step S30, the displaying equipment 1 may automatically reset the primary system module 103 whenever the primary system module 103 is determined to be abnormal, thereby marking the primary system module 103 to restore to a normal status as soon as possible.

After the step S28 and the step S30, the system controlling module 102 and/or the image controlling module 101 determine whether the displaying equipment 1 is turned off or not (step S32), and re-execute the step S12 through the step S30 before the displaying equipment 1 is turned off. Therefore, the displaying equipment 1 may continuously provide and display the input image 31 before the primary system module 103 recovers to a normal status, and may provide and display both the input image 31 and the processed image 32 simultaneously after the primary system module 103 recovers to the normal status. By using the above technical solution, the user may be assured not to be affected by the status of the primary system module 103.

In one embodiment, the step S26 is to determine whether the primary system module 103 is abnormal or not by the system controlling module 102. In particular, the system controlling module 102 may execute the watchdog procedure after it activates completely, or periodically perform the handshaking procedure with the primary system module 103, so as to monitor the primary system module 103. After the primary system module 103 activates completely, the primary system module 103 may receive an inquiring signal sent by the system controlling module 102, and may make a response to the inquiring signal.

If the system controlling module 102 cannot receive a response from the primary system module 103 after sending the inquiring signal, and the non-respond status of the primary system module 103 meets a preset threshold condition, the system controlling module 102 may determine that the primary system module 103 is abnormal. The present threshold condition may be, for example but not limited to, slow response, no response and more than a certain number of times, or no response and lasting longer than a certain time period, etc.

In another embodiment, the step S26 is to determine whether the primary system module 103 is abnormal by the image controlling module 101. As discussed, the image controlling module 101 may start to transmit the input image 31 to the primary system module 103 after the primary system module 103 activates completely, and to continuously receive the processed image 32 transmitted from the primary system module 103. In the embodiment, the image controlling module 101 may analyze the processed image 32 after receiving the processed image 32. When the primary system module 103 stops transmitting the processed image 32 or the processed image 32 is analyzed to be frozen, the image controlling module 101 may determine that the primary system module 103 is abnormal.

It should be mentioned that the processed image 32 is an image that has been analyzed, corrected, or edited by the algorithm(s) or application program(s) of the primary system module 103, and the processed image 32 carries more details in comparison with the input image 31. In addition to display the input image 31 and the processed image 32 simultaneously, the displaying equipment 1 may also adjust the display mode of the images in accordance with the operation made by the user.

Please refer to FIG. 1 through FIG. 4, wherein FIG. 4 is a schematic diagram of a displaying equipment of a second embodiment according to the present disclosure. In the embodiment, the image output unit 11 may be a touch screen. The image output unit 11 may send out a control signal after accepting an operation made by the user. The system controlling module 102 may receive the control signal through the image controlling module 101, and adjust the displaying parameters of the image controlling module 101 correspondingly based on the content of the control signal. The displaying parameters may be, for example but not limited to, parameters indicate the user's actions such as selection, dragging, zoom-in, or zoom-out, etc.

Through the operation, the user may change the display mode of the displaying equipment 1 in displaying the input image 31 and/or the processed image 32. The embodiment of FIG. 4 depicts an example that enlarging the processed image 32 and adjusting the display mode to a superimposed display mode, so the user may obtain more image information from the processed image 32. In particular, the user may designate the priority of different images 31, 32. When the user enlarges, reduces, or drags each of the images 31, 32 through the operation, the image having a smaller priority may be covered below another image having a greater priority. Therefore, the user may adjust the display mode for the multiple images 31, 32 on demand.

In another embodiment, the displaying equipment 1 may include one or more signal input ports 13 connected with the image controlling module 101. In this embodiment, the displaying equipment 1 may connect to, through the signal input port(s) 13, an external device such as a keyboard, a mouse, a touch pad, a remote control, or an external touch screen, etc. (not shown). The signal input port 13 may be a universal serial bus (USB) connecting port, but not limited thereto.

In the embodiment, the user may operate the external device to send a control signal to the system controlling module 102. The system controlling module 102 may adjust the aforementioned displaying parameters of the image controlling module 101 based on the content of the control signal. In other words, by operating the external device, the user may change the display mode of the displaying equipment 1 in displaying the input image 31 and/or the processed image 32.

It should be mentioned that the user may send an editing command for the image through the image output unit 11 or an external device as well. For example, the user may perform actions like labeling, coloring, or making a snapshot of the image. Under such circumstance, the system controlling module 102 may receive the editing command through the image controlling module 101, and transmit the editing command to the primary system module 103. Therefore, the primary system module 103 may control the executed algorithm(s) or application program(s) in accordance with the editing command, so that the primary system module 103 may ensure that the processed image 32 is satisfying the operation made by the user.

In the above embodiment, the image input port 12, the signal input port 13, and the image output unit 11 are connected with the image controlling module 101, and the system controlling module 102 receives the signal outputted from the image input port 12, the signal input port 13, and the image output unit 11 through the image controlling module 101. In other words, the image controlling module 101 operates as a communication bridge between the system controlling module 102 and peripheral devices.

In another embodiment, the image input port 12, the signal input port 13, and the image output unit 11 may respectively connect to the system controlling module 102 through an I²C interface or an SPI interface, so as to directly transmit the signal to the system controlling module 102.

As discussed above, the displaying equipment 1 of the present disclosure may be used under an emergency medical situation. It is known by the public that in addition to the urgent time, the environment is usually limited while performing an emergency medical action (such as to perform a first-aid in an ambulance). With the environment being restricted, the user may be unable to put the displaying equipment 1 or an external displayer connected with the displaying equipment 1 correctly, and it may cause the inconvenient for the user when checking the images.

Figure 5A:
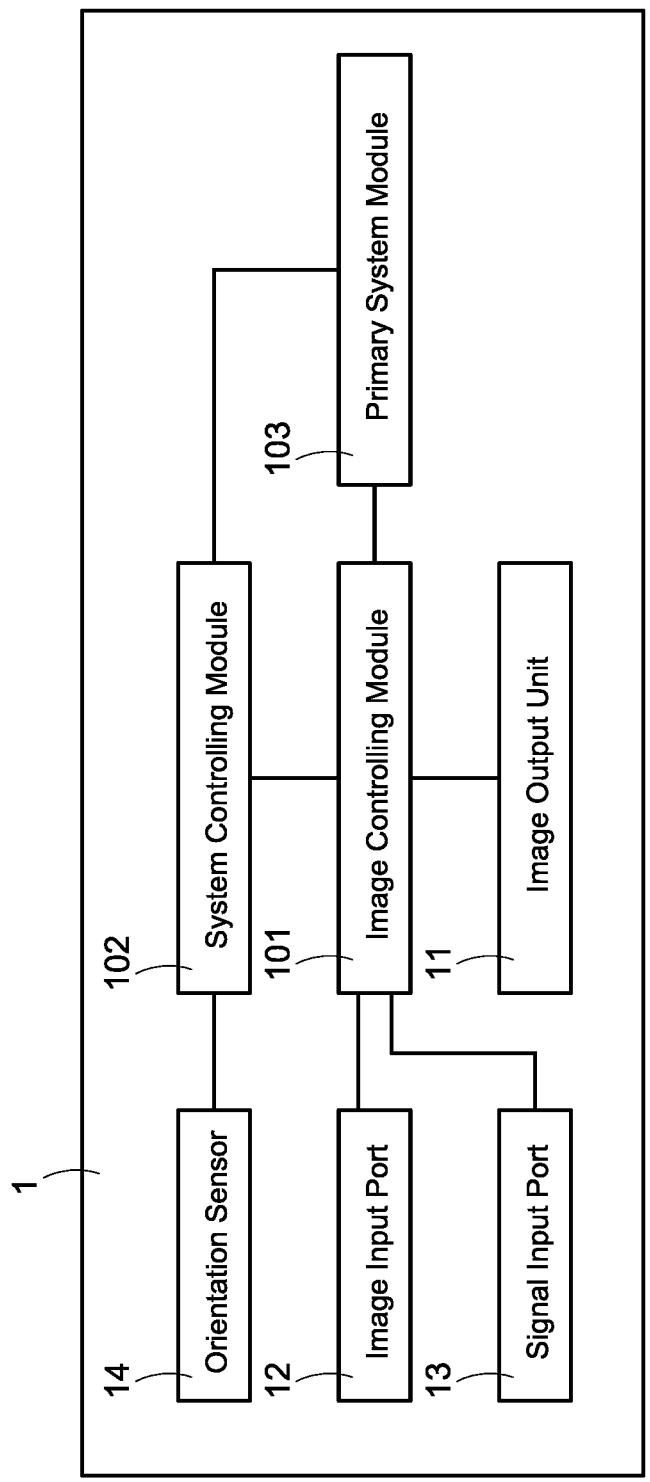
FIG. 5A is a block diagram of a displaying equipment of a second embodiment according to the present disclosure.
Figure 5B:
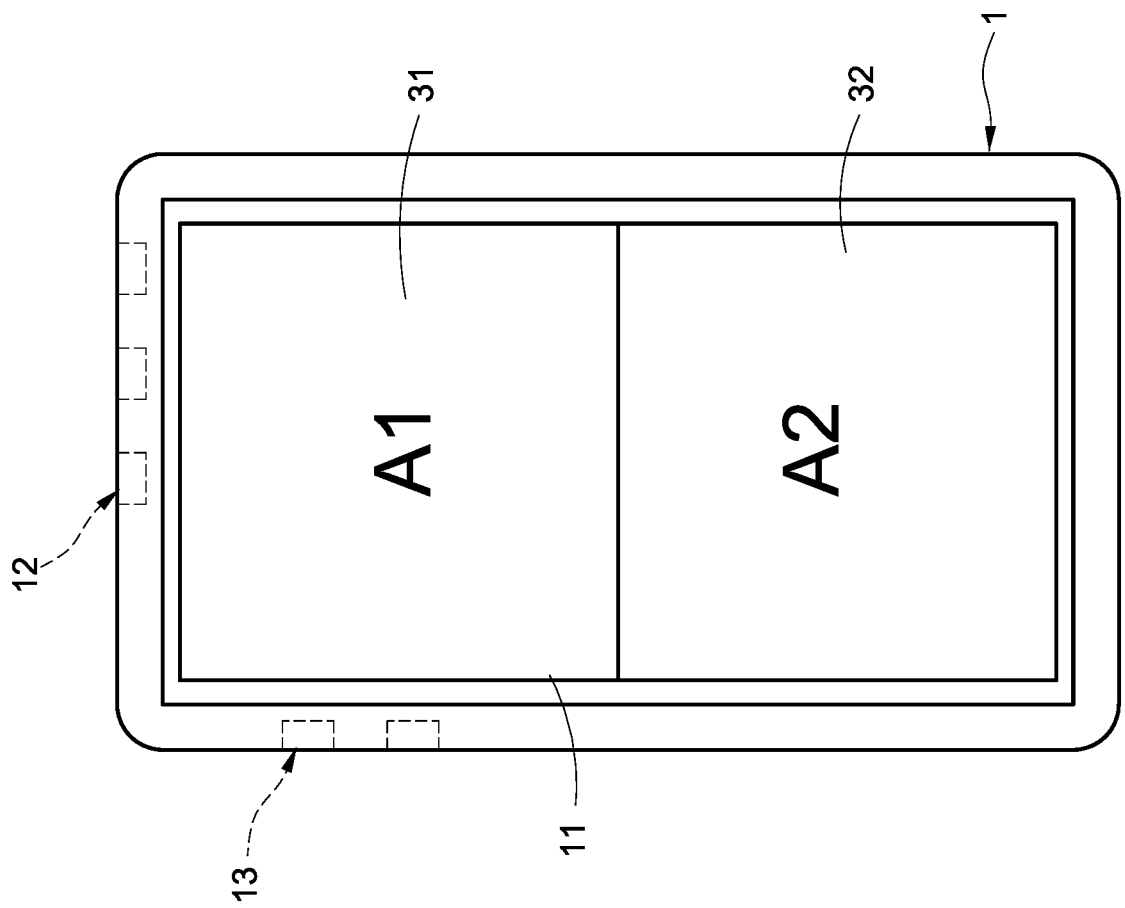
FIG. 5B is a schematic diagram of a displaying equipment of a third embodiment according to the present disclosure.

Please refer to FIG. 5A and FIG. 5B at the same time, wherein FIG. 5A is a block diagram of a displaying equipment of a second embodiment according to the present disclosure, and FIG. 5B is a schematic diagram of a displaying equipment of a third embodiment according to the present disclosure.

As disclosed in FIG. 5A, the displaying equipment 1 of the present disclosure may include an orientation sensor 14 electrically connected with the system controlling module 102. The orientation sensor 14 is configured to sense a rotated angle of the displaying equipment 1. In one embodiment, the orientation sensor 14 may be a G-sensor or an accelerometer, but not limited thereto.

As disclosed in FIG. 5B, the displaying equipment 1 may sense the rotated angle of itself by the orientation sensor 14, and transmit the rotated angle to the system controlling module 102. Therefore, the system controlling module 102 may adjust the displaying parameter(s) of the image controlling module 101 based on the rotated angle, so as to adjust the displaying direction of the input image 31 and the processed image 32. Therefore, no matter how the user put the displaying equipment 1, the user may always see the input image 31 and the processed image 32 being displayed in a correct direction and in a correct angle through the image output unit 11.

In another embodiment, the image output unit 11 is a video connecting port, and the displaying equipment 1 connects with an external displayer through the image output unit 11. If the external displayer is embedded with a same or similar orientation sensor, the system controlling module 102 of the displaying equipment 1 may receive the rotated angle transmitted from the external displayer through the image controlling module 11, and adjust the displaying parameter(s) of the image controlling module 101, so as the adjust the displaying direction of the input image 31 and the processed image 32 being displayed on the external displayer.

By displaying the input image 31 and the processed image 32 in the correct direction and the correct angle, the convenience of using the displaying equipment 1 under an emergency medical action may be effectively improved.

Figure 6:
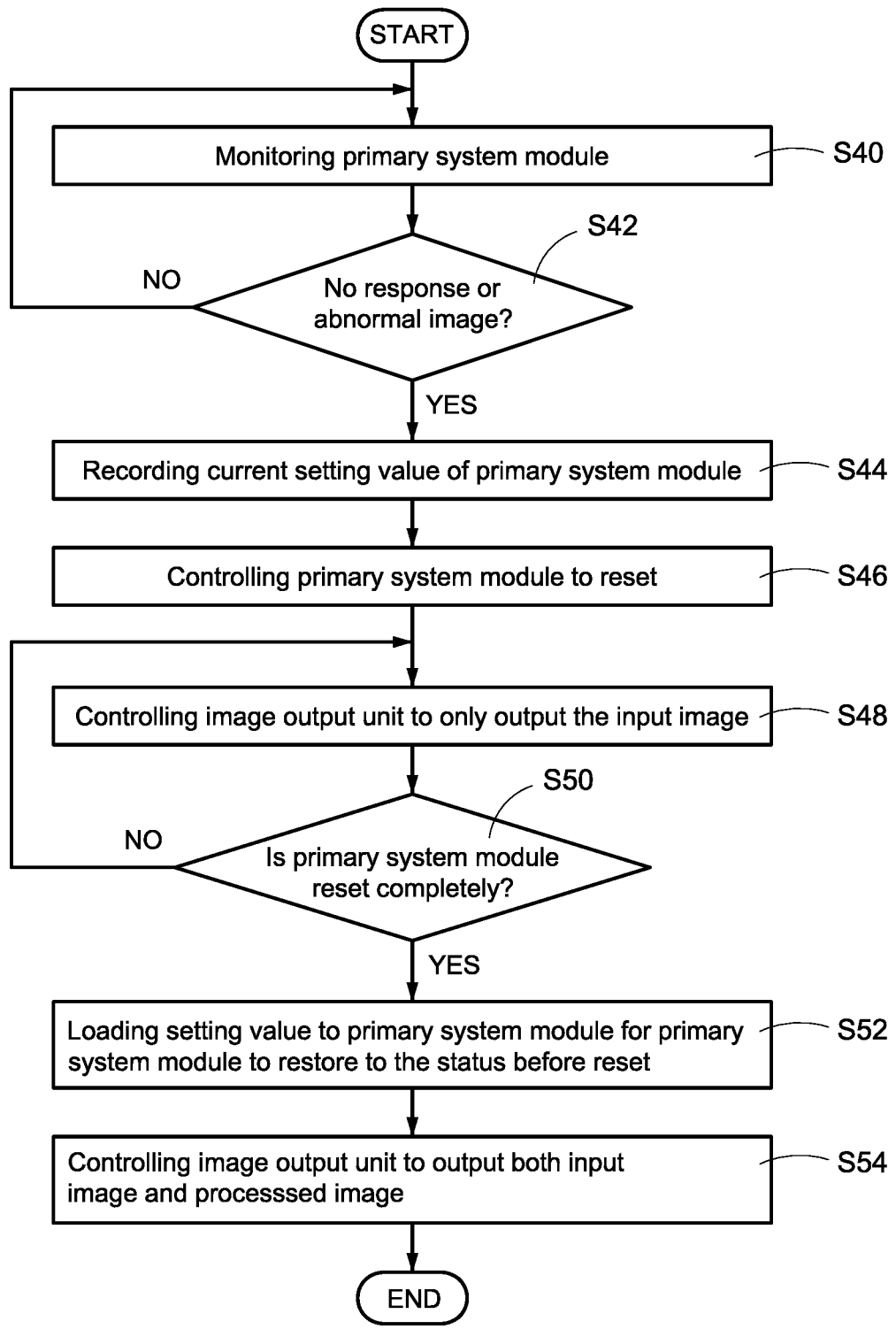
FIG. 6 is a flowchart of a displaying method of a second embodiment according to the present disclosure.

Please refer to FIG. 1, FIG. 2, FIG. 3A, FIG. 3B, and FIG. 6 at the same time, wherein FIG. 6 is a flowchart of a displaying method of a second embodiment according to the present disclosure.

In the present disclosure, after the primary system module 103 activates completely, the displaying equipment 1 continuously monitors the primary system module 103 by the system controlling module 102 and/or the image controlling module 101 (step S40). In particular, the system controlling module 102 of the displaying equipment 1 periodically determines whether a response from the primary system module 103 is received; otherwise, the image controlling module 101 of the displaying equipment 1 continuously determines whether the image transmitted from the primary system module 103 is abnormal (step S42).

If the primary system module 103 normally responds to the calling of the system controlling module 102 (i.e., a responsed from the primary system module 103 is received), and normally transmits the processed image 32 to the image controlling module 101, it indicates that the primary system module 103 operates normally. Under such circumstance, the displaying equipment 1 does not perform an additional control to the primary system module 103, and the displaying equipment 1 continuously monitors the primary system module 103 by the system controlling module 102 and/or the image controlling module 101. In the meantime, the image controlling module 101 continuously outputs the input image 31 and the processed image 32 through the image output unit 11.

In the step S42, if the system controlling module 102 determines that the primary system module 103 does not respond (i.e., no response from the primary system module 103 is received), or the image controlling module 101 determines that the image transmitted from the primary system module 103 is abnormal, it indicates that the primary system module 103 is abnormal or becoming abnormal soon. Under such circumstance, the displaying equipment 1 records current setting value(s) of the primary system module 103 by the system controlling module 102 (step S44), and controls the primary system module 103 to reset (step S46).

In particular, after the primary system module 103 activates completely, it performs essential setting to its OS, algorithm(s), and application program(s) respectively and records relevant setting values respectively. The setting values may be recorded either in a register (not shown) of the displaying equipment 1, in the system controlling module 102, or in the image controlling module 101, but not limited. In addition, after the OS, the algorithm(s), or the application program(s) is adjusted, the primary system module 103 further records the adjusted setting values as well.

In the present disclosure, the system controlling module 102 records the setting values of the primary system module 103 while monitoring the primary system module 103. In particular, when the system controlling module 102 or the image controlling module 101 determines that the primary system module 103 is abnormal in the step S42, the system controlling module 102 obtains the current setting values of the primary system module 103 (e.g., to obtain the latest setting values recorded before the primary system module 103 is determined to be abnormal either from the register, from the system controlling module 102, or from the image controlling module 101), and controls the primary system module 103 to reset.

After the primary system module 103 is determined to be abnormal, the image controlling module 101 controls the image output unit 11 to switch to a display mode of only outputting the input image 31 received from the image sensitive device 2 (step S48). Therefore, while the primary system module 103 is abnormal and is resetting, the user may still obtain the input image 31 from the displaying equipment 1 without being affected by the abnormal status of the primary system module 103.

It should be mentioned that the step S46 and the step S48 do not have an execution order, the displaying equipment 1 may first control the primary system module 103 to reset by the system controlling module 102, and then switch the display mode of the images by the image controlling module 101. Else, the displaying equipment 1 may first switch the display mode of the images by the image controlling module 101, and then control the primary system module 103 to reset by the system controlling module 102. In another embodiment, the displaying equipment 1 may execute the step S46 and the step S48 at the same time through multi-tasking technique, and not limited to the order disclosed in FIG. 6.

After the step S46 and the step S48, the system controlling module 102 keeps determining whether the primary system module 103 is reset completely (step S50), and keeps the image output unit 11 to only output the input image 31 before the primary system module 103 is reset completely.

In one embodiment, the system controlling module 102 may continuously execute the watchdog procedure or the handshaking procedure with the primary system module 103 while resetting the primary system module 103, and determine that the primary system module 103 is reset completely once a response from the primary system module 103 is received.

After the primary system module 103 is reset completely, the system controlling module 102 transmits the setting values obtained in the step S44 to the primary system module 103, and to load the setting values to the primary system module 103 in order that the primary system module 103 may restore to a status before reset (step S52).

After the step S52, the system controlling module 102 notifies the image controlling module 101 that the primary system module 103 is reset completely, or the primary system module 103 itself sends an image requirement to the image controlling module 101. Therefore, the image controlling module 101 starts to transmit the input image 31 to the primary system module 103, and to receive the processed image 32 transmitted from the primary system module 103. In addition, the image controlling module 101 controls the image output unit 11 to switch to a display mode of outputting both the input image 31 and the processed image 32 at the same time (step S54).

It should be mentioned that the primary system module 103 in the present disclosure is used to execute the OS and the application program(s), so as to perform the image processing procedure(s) to the input image 31. As a result, the primary system module 103 consumes electricity more than the image controlling module 101 and the system control module 102 do.

In one embodiment, the displaying equipment 1 may operate through using a battery. When determining that the power of the battery is insufficient, the displaying equipment 1 may control the primary system module 103 to enter a sleep mode by the system controlling module 102, and control the image output unit 11 to display the input image 31 alone. Therefore, the power of the displaying equipment 1 may be saved, so as to prevent the user from losing the images during the emergency medical action.

In the embodiment, the displaying equipment 1 may control the system controlling module 102 to reset the primary system module 103 after the user changes the battery for the displaying equipment 1 or connects the displaying equipment 1 to an external power source, so that the image output unit 11 may restore to a display mode of displaying both the input image 31 and the processed image simultaneously. By using the above technical solution, the output of the displaying equipment 1 may be kept stably to improve the quality of medical actions.

By using the technical solution of the present disclosure, the displaying equipment 1 may display the input image 31 sensed and generated by the image sensitive device 2 immediately right after it receives power and boots, and display both the input image 31 and the processed image 32 simultaneously right after the primary system module 103 activates completely. Therefore, the purpose of providing quick displaying mechanism may be achieved. In addition, the displaying equipment 1 may keep displaying the input image 31 and automatically reset the primary system module 103 whenever the primary system module 103 is determined to be abnormal, and the displaying equipment 1 may restore to a display mode of displaying both the input image 31 and the processed image 32 after the primary system module 103 is reset completely. Therefore, the purpose of having a system-failure backup mechanism may be achieved. In other words, the displaying equipment 1 of the present disclosure may assist the user to obtain the demanded images as soon as possible, and keep providing the images to satisfy the image requirement of the user under the emergency medical actions.

As the skilled person will appreciate, various changes and modifications can be made to the described embodiment. It is intended to include all such variations, modifications and equivalents which fall within the scope of the present disclosure, as defined in the accompanying claims.

What is claimed is:

1. A displaying equipment capable of quick displaying and system-failure backup mechanism, comprising:
    an image input port, connected to an image sensitive device to continuously receive an input image;
    an image output unit;
    an image controlling module, connected with the image input port and the image output unit, and configured to continuously receive the input image from the image input port and immediately control the image output unit to continuously output the input image after the image controlling module activates completely;

a primary system module, connected with the image controlling module, configured to run an operating system (OS) after being activated, and configured to perform an image processing procedure to the input image to generate a processed image, and to continuously transmits the processed image to the image controlling module, wherein an activation completing time of the primary system module is later than or equal to an activation completing time of the image controlling module; and a system controlling module, connected with the image controlling module and the primary system module, configured to continuously monitor the primary system module after the system controlling module activates completely;

wherein, the image controlling module is configured to control the image output unit to output both the input image and the processed image after receiving the processed image, and configured to control the image output unit to only output the input image when the primary system module is determined to be abnormal.

2. The displaying equipment in claim 1, wherein the image output unit is a displaying unit or a video connecting port used to connected to an external displayer, wherein the video connecting port is a high-definition multimedia interface (HDMI) connecting port, a serial digital interface (SDI) connecting port, or a DisplayPort connecting port.

3. The displaying equipment in claim 2, further comprising an orientation sensor electrically connected with the system controlling module, wherein the orientation sensor is configured to sense a rotated angle of the displaying equipment, and the system controlling module is configured to control the image controlling module in accordance with the rotated angle to adjust a displaying direction and a displaying angle of the input image and the processed image.

4. The displaying equipment in claim 1, wherein the image controlling module is a field programmable gate array (FPGA) or an application specific integrated circuit (ASIC), the primary system module is a central process unit (CPU) or a graphic process unit (GPU), and the system controlling module is a micro control unit (MCU) or an embedded controller (EC).

5. The displaying equipment in claim 1, further comprising a signal input port electrically connected with the image controlling module, wherein the system controlling module is configured to obtain a control signal of the signal input port through the image controlling module, and to adjust a displaying parameter of the image controlling module in accordance with a content of the control signal.

6. The displaying equipment in claim 1, wherein the input image and the processed image are displayed side by side or superimposed displayed.

7. The displaying equipment in claim 1, wherein the system controlling module is configured to execute a watchdog procedure or to periodically execute a handshaking procedure with the primary system module to monitor the primary system module, and is configured to determine that the primary system module is abnormal if no response from the primary system module is received and a preset threshold condition is met.

8. The displaying equipment in claim 1, wherein the image controlling module is configured to determine that the primary system module is abnormal when the primary system module stops transmitting the processed image or the processed image is determined to be frozen.

9. The displaying equipment in claim 1, wherein the system controlling module is configured to record a current setting value of the primary system module when the primary system module is determined to be abnormal and to control the primary system module to reset, and the system controlling module is configured to load the setting value to the primary system module for the primary system module to restore to a status before reset after the primary system module is reset completely.

10. A displaying method capable of quick displaying and system-failure backup mechanism, incorporated with a displaying equipment having an image controlling module, a primary system module, and a system controlling module, comprising:

a) continuously monitoring the primary system module by the system controlling module after the system controlling module activates completely;

b) continuously receiving an input image from an image sensitive device and immediately controlling an image output unit to continuously output the input image by the image controlling module after the image controlling module activates completely;

c) running an operating system (OS) by the primary system module after the primary system module is activated, wherein an activation completing time of the primary system module is later than or equal to an activation completing time of the image controlling module;

d) continuously receiving the input image from the image controlling module, executing an image processing procedure to the input image to generate a processed image, and continuously transmitting the processed image to the image controlling module by the OS;

e) controlling the image output unit to output both the input image and the processed image by the image controlling module after receiving the processed image;

f) determining whether the primary system module is abnormal; and g) controlling the image output unit to only output the input image by the image controlling module when the primary system module is determined to be abnormal.

11. The displaying method in claim 10, wherein the image controlling module is a field programmable gate array (FPGA) or an application specific integrated circuit (ASIC), the primary system module is a central process unit (CPU) or a graphic process unit (GPU), and the system controlling module is a micro control unit (MCU) or an embedded controller (EC).

12. The displaying method in claim 10, wherein the step f) comprises executing a watchdog procedure or periodically executing a handshaking procedure with the primary system module by the system controlling module, and determining that the primary system module is abnormal when no response from the primary system module is received and a preset threshold condition is met.

13. The displaying method in claim 10, wherein the step f) comprises determining that the primary system module is abnormal when detecting that the primary system module stops transmitting the processed image or the processed image is determined to be frozen.

14. The displaying method in claim 10, further comprises:

h) recording a current setting value of the primary system module when the primary system module is determined to be abnormal;

i) controlling the primary system module to reset by the system controlling module;

j) continuously determining whether the primary system module is reset completely by the system controlling module after the step i);

k) loading the setting value to the primary system module for the primary system module to restore to a status before reset after the primary system module is reset completely; and l) re-executing the step d) and the step e) after the step k).

* * * * *